United States Patent
Gao et al.

(10) Patent No.: US 9,589,374 B1
(45) Date of Patent: Mar. 7, 2017

(54) COMPUTER-AIDED DIAGNOSIS SYSTEM FOR MEDICAL IMAGES USING DEEP CONVOLUTIONAL NEURAL NETWORKS

(71) Applicant: 12 Sigma Technologies, San Diego, CA (US)

(72) Inventors: Dashan Gao, San Diego, CA (US); Xin Zhong, San Diego, CA (US)

(73) Assignee: 12 SIGMA TECHNOLOGIES, San Diego, CA (US)

( * ) Notice: Subject to any disclaimer, the term of this patent is extended or adjusted under 35 U.S.C. 154(b) by 0 days.

(21) Appl. No.: 15/225,597

(22) Filed: Aug. 1, 2016

(51) Int. Cl.
| | |
|---|---|
| G06K 9/00 | (2006.01) |
| G06T 11/00 | (2006.01) |
| G06T 7/00 | (2006.01) |
| A61B 5/055 | (2006.01) |
| A61B 5/00 | (2006.01) |
| A61B 6/03 | (2006.01) |
| A61B 6/00 | (2006.01) |
| A61B 8/00 | (2006.01) |

(52) U.S. Cl.
CPC ............ *G06T 11/008* (2013.01); *A61B 5/055* (2013.01); *A61B 5/4312* (2013.01); *A61B 6/032* (2013.01); *A61B 6/037* (2013.01); *A61B 6/504* (2013.01); *A61B 8/00* (2013.01); *G06T 7/0012* (2013.01); *G06T 7/0081* (2013.01); *G06T 11/005* (2013.01); *G06T 2207/10072* (2013.01); *G06T 2207/20084* (2013.01); *G06T 2207/20148* (2013.01); *G06T 2207/30004* (2013.01)

(58) Field of Classification Search
CPC ... G06T 11/008; G06T 11/005; G06T 7/0012; G06T 7/0081; G06T 2207/10072; G06T 2207/20084; G06T 2207/20148; G06T 2207/30004; A61B 5/0055; A61B 5/4312; A61B 6/0032; A61B 6/037; A61B 6/504; A61B 8/00
USPC ................................................. 382/128, 154
See application file for complete search history.

(56) References Cited

U.S. PATENT DOCUMENTS

| | | | | |
|---|---|---|---|---|
| 2015/0238148 | A1* | 8/2015 | Georgescu | A61B 5/7267 600/408 |
| 2016/0078614 | A1* | 3/2016 | Ryu | G06T 7/0012 382/128 |
| 2016/0174902 | A1* | 6/2016 | Georgescu | A61B 5/7267 600/408 |

OTHER PUBLICATIONS

Ciresan et al. Deep Neural Networks Segment Neuronal Membranes in Electron Microscopy Images. Advances in Neural Information Processing Systems 25 (NIPS 2012) (9 pgs.).
Firmino et al. Computer-aided detection system for lung cancer in computed tomography scans: Review and future prospects. BioMedical Engineering OnLine 13:41 (2014).
Roth et al. A New 2.5D Representation for Lymph Node Detection using Random Sets of Deep Convolutional Neural Network Observations. Medical Image Computing and Computer-Assisted Intervention—8673:520-527 (MICCAI 2014) (14 pgs).
Setio et al. Pulmonary Nodule Detection in CT Images: False Positive Reduction Using Multi-View Convolutional Networks. IEEE Transactions on Medical Imaging 35(5):1160-1169 (2016).

(Continued)

*Primary Examiner* — Tom Y Lu
(74) *Attorney, Agent, or Firm* — Wilson, Sonsini, Goodrich & Rosati

(57) ABSTRACT

Described are systems, media, and methods for applying deep convolutional neural networks to medical images to generate a real-time or near real-time diagnosis.

30 Claims, 7 Drawing Sheets

(56) References Cited

OTHER PUBLICATIONS

Shen et al. Chapter 46: Multi-scale Convolutional Neural Networks for Lung Nodule Classification. Information Processing in Medical Imaging. 9123:588-599 (2015).
Suzuki. A supervised 'lesion-enhancement' filter by use of a massive-training artificial neural network (MTANN) in computer-aided diagnosis (CAD). Phy Med Biol S4(18):S31-S45 (2009).

* cited by examiner

COMPUTER-AIDED DIAGNOSIS SYSTEM FOR MEDICAL IMAGES USING DEEP CONVOLUTIONAL NEURAL NETWORKS

BACKGROUND OF THE INVENTION

Disease diagnosis is an important step in health examination. Medical imaging is a useful tool to diagnose many diseases and offers noninvasive diagnoses, which are a greater advantage than other tools. However, medical imaging generates a large volume of data, and analyzing medical images takes a long process. In early stage of disease diagnoses, abnormal tissues may not be prominent even under high resolution imaging modalities. Thus, new technologies to address the issues are necessary.

SUMMARY OF THE INVENTION

Computer Aided Diagnostic (CAD) systems for medical images aim to help doctors diagnose diseases more efficiently, by reducing examination time, increasing diagnostic accuracy, and reduce diagnostic variations due to experiences and personal conditions. Using advanced computer technology, a CAD system highlights regions of potential medical conditions for doctors to scrutinize and to make final diagnostic decisions. The present disclosure offers a successful CAD system with a high sensitivity and selectivity such that all possible anomalies are detected without including many misclassified regions.

A CAD system may rely on manually crafted features to describe unhealthy tissues. Some examples of such features include intensity, edge, 2D/3D curvature, shape, and other 2D/3D geometric characteristics. Designing such features may involve a lot of domain knowledge to the specific problem, although mostly it is still very heuristic. Once a feature is considered, it is hard to adapt to new data and cases. As a result, the system often suffers from low detection rate and high false positive, and cannot meet the requirements of clinical use. Further, another problem of a traditional CAD system is slow processing speed. Many traditional CAD systems take a long time for data processing. However, some applications and medical procedures (e.g., computer-guided surgery) require obtaining real-time or near real-time results.

The present disclosure addresses the difficulties by a real-time automatic image analysis. To create a faster processing, the technologies disclosed herein segment a region of interest, and the following processing is applied to the region rather than to the entire image domain. Further, an initial screening is performed on individual 2D slices rather on the 3D volumetric space, in order to conserve computational resources. Next, a refined detection step is applied on the initial screening results. The segmentation and the cascaded process allow fast processing, and achieve real-time or near real-time results. On the other hand, to achieve high accuracy, the disclosed technologies utilize convolutional neural networks with randomized optimization. The disclosed technologies include deep learning-based solution, such as deep (multi-layer) convolutional neural networks (DCNN), to automatically learn critical features and their characteristics about a disease, by scanning through large amounts of expert-labeled medical images. The automatically learned features are more discriminative than manually selected features, and can more easily adapt to new data/cases.

In one aspect, disclosed herein is a computer-implemented system comprising: a digital processing device comprising: at least one processor, an operating system configured to perform executable instructions, a memory, and a computer program including instructions executable by the digital processing device to create an application applying deep convolutional neural networks to medical images to generate a real-time or near real-time diagnosis or diagnostic recommendation, the application comprising: (a) a software module performing image segmentation of a plurality of medical images, the image segmentation comprising isolating a region of interest from each image; (b) a software module applying a cascaded deep convolutional neural network detection structure to the segmented images, the detection structure comprising: (1) a first stage employing a first convolutional neural network to screen all possible locations in each 2D slice of the segmented medical images by a sliding window methodology to identify one or more candidate locations; and (2) a second stage employing a second convolutional neural network to screen 3D volumes constructed from the candidate locations by selecting at least one random location within each volume with a random scale and a random viewing angle to identify one or more refined locations and classifying the refined locations; and (b) a software module automatically generating a report comprising a diagnosis or diagnostic recommendation. In some embodiments, the medical images are from a CT scan, a PET/CT scan, a SPECT scan, an MRI, an ultrasound, an X-ray, a mammogram, an angiogram, a fluorogram, a microgram, or a combination thereof. In some embodiments, the application further comprises a software module performing image preprocessing comprising normalization of the plurality of medical images. In some embodiments, the normalization comprises normalization of image format, image slice spacing, image intensity, image contract, and image orientation. In some embodiments, the images are normalized to DICOM format, NIfTI format, or raw binary format. In some embodiments, the region of interest is an organ, a part of an organ, or a tissue. In some embodiments, the candidate locations comprise less than 10% of the locations in the 2D slices of the segmented medical images. In some embodiments, the first convolutional neural network has 2-20 convolutional layers and 1-10 fully connected layers. In some embodiments, the first convolutional neural network has 3-8 convolutional layers and 3-5 fully connected layers. In some embodiments, the sliding window is a window of less than 100 pixels by less than 100 pixels. In some embodiments, the sliding window is a window of 10-40 pixels by 10-40 pixels. In some embodiments, the sliding window is a window of about 31 pixels by about 31 pixels. In some embodiments, the sliding window is a window of about 16 pixels by about 16 pixels. In some embodiments, the first convolutional neural network comprises at least one neural network instance selected randomly from a plurality of neural network instances. In some embodiments, the second convolutional neural network has five or more convolutional and fully connected layers. In some embodiments, the 3D volumes are less than 100 pixels in each direction. In further embodiments, the 3D volumes are 10-40 pixels in each direction. In still further embodiments, the 3D volumes are about 32 pixels in each direction. In some embodiments, the 3D volumes are about 16 pixels in each direction. In some embodiments, the second convolutional neural network selects a plurality of random locations within each volume. In some embodiments, the second convolutional neural network selects a plurality of random scales at each location. In some embodiments, the second convolutional neural network selects a plurality of random viewing angles for each location. In some embodiments, the second convolutional neural network comprises at least one neural network instance selected randomly from a plurality of neural network instances. In some embodiments, the application further comprises a software module performing post-processing of the refined locations. In further embodiments, the post-processing comprises characterizing one or more of: centroid location, volume, shape, intensity, density, transparency, and regularity. In still further embodiments, the post-processing comprises determination whether two or more refined locations are parts of the same disease site. In some embodiments, wherein the application runs in real-time or near real-time and generates a real-time or near real-time diagnosis or diagnostic recommendation. In some embodiments, the diagnosis or diagnostic recommendation comprises a determination whether any locations are disease sites. In some embodiments, the report comprises an informational overlay on one or more of the medical images. In further embodiments, the overlay comprises a point location indictor, an area indicator, or a contour indicator. In some embodiments, the report comprises one or more medical images color-coded to indicate disease type. In some embodiments, the report comprises one or more medical images heat mapped to indicate diagnostic confidence level. In some embodiments, the report comprises a time course generated by applying the application to medical images captured at two or more time points. In some embodiments, the first and second convolutional neural networks are trained to identify critical clinical signs of a disease. In further embodiments, the first and second convolutional neural networks are trained using medical images labeled by a human expert and subjected to preprocessing to normalize image format, image slice spacing, image intensity, image contract, and image orientation. In some embodiments, the first and second convolutional neural networks are trained using medical images balanced for normal and disease locations.

In another aspect, disclosed herein are non-transitory computer-readable storage media encoded with a computer program including instructions executable by a processor to create an application applying deep convolutional neural networks to medical images to generate a real-time or near real-time diagnosis or diagnostic recommendation, the application comprising: (a) a software module performing image segmentation of a plurality of medical images, the image segmentation comprising isolating a region of interest from each image; (b) a software module applying a cascaded deep convolutional neural network detection structure to the segmented images, the detection structure comprising: (1) a first stage employing a first convolutional neural network to screen all possible locations in each 2D slice of the segmented medical images by a sliding window methodology to identify one or more candidate locations; and (2) a second stage employing a second convolutional neural network to screen 3D volumes constructed from the candidate locations by selecting at least one random location within each volume with a random scale and a random viewing angle to identify one or more refined locations and classifying the refined locations; and (c) a software module automatically generating a report comprising a diagnosis or diagnostic recommendation. In some embodiments, the medical images are from a CT scan, a PET/CT scan, a SPECT scan, an MM, an ultrasound, an X-ray, a mammogram, an angiogram, a fluorogram, a microgram, or a combination thereof. In some embodiments, the application further comprises a software module performing image preprocessing comprising normalization of the plurality of medical images. In some embodiments, the normalization comprises normalization of image format, image slice spacing, image intensity, image contract, and image orientation. In some embodiments, the images are normalized to DICOM format, NIfTI format, or raw binary format. In some embodiments, the region of interest is an organ, a part of an organ, or a tissue. In some embodiments, the candidate locations comprise less than 10% of the locations in the 2D slices of the segmented medical images. In some embodiments, the first convolutional neural network has 2-20 convolutional layers and 1-10 fully connected layers. In some embodiments, the first convolutional neural network has 3-8 convolutional layers and 3-5 fully connected layers. In some embodiments, the sliding window is a window of less than 100 pixels by less than 100 pixels. In some embodiments, the sliding window is a window of 10-40 pixels by 10-40 pixels. In further embodiments, the sliding window is a window of about 31 pixels by about 31 pixels. In further embodiments, the sliding window is a window of about 16 pixels by about 16 pixels. In some embodiments, the first convolutional neural network comprises at least one neural network instance selected randomly from a plurality of neural network instances. In some embodiments, the second convolutional neural network has five or more convolutional and fully connected layers. In some embodiments, the 3D volumes are less than 100 voxels in each direction. In some embodiments, the 3D volumes are 10-40 voxels in each direction. In some embodiments, the 3D volumes are about 32 voxels in each direction. In some embodiments, the 3D volumes are about 16 voxels in each direction. In some embodiments, the second convolutional neural network selects a plurality of random locations within each volume. In some embodiments, the second convolutional neural network selects a plurality of random scales at each location. In some embodiments, the second convolutional neural network selects a plurality of random viewing angles for each location. In some embodiments, the second convolutional neural network comprises at least one neural network instance selected randomly from a plurality of neural network instances. In some embodiments, the application further comprises a software module performing post-processing of the refined locations. In some embodiments, the post-processing comprises characterizing one or more of: centroid location, volume, shape, intensity, density, transparency, and regularity. In some embodiments, the post-processing comprises determination whether two or more refined locations are parts of the same disease site. In some embodiments, the application runs in real-time or near real-time and generates a real-time or near real-time diagnosis or diagnostic recommendation. In some embodiments, the diagnosis or diagnostic recommendation comprises a determination whether any locations are disease sites. In some embodiments, the report comprises an informational overlay on one or more of the medical images. In some embodiments, the overlay comprises a point location indictor, an area indicator, or a contour indicator. In some embodiments, the report comprises one or more medical images color-coded to indicate disease type. In some embodiments, the report comprises one or more medical images heat mapped to indicate diagnostic confidence level. In some embodiments, the report comprises a time course generated by applying the application to medical images captured at two or more time points. In some embodiments, the first and second convolutional neural networks are trained to identify critical clinical signs of a disease. In some embodiments, the first and second convolutional neural networks are trained using medical images labeled by a human expert and subjected to preprocessing to normalize image format, image slice spacing, image intensity, image contract, and image orientation. In some embodiments, the first and second convolutional neural networks are trained using medical images balanced for normal and disease locations.

In yet another aspect, disclosed is a computer-implemented method of applying deep convolutional neural networks to medical images to generate a real-time or near real-time diagnosis or diagnostic recommendation comprising: (a) performing, by a computer, image segmentation of a plurality of medical images, the image segmentation comprising isolating a region of interest from each image; (b) applying, by the computer, a cascaded deep convolutional neural network detection structure to the segmented images, the detection structure comprising: (1) a first stage employing a first convolutional neural network to screen all possible locations in each 2D slice of the segmented medical images by a sliding window methodology to identify one or more candidate locations; and (2) a second stage employing a second convolutional neural network to screen 3D volumes constructed from the candidate locations by selecting at least one random location within each volume with a random scale and a random viewing angle to identify one or more refined locations and classifying the refined locations; and (c) automatically generating, by the computer, a report comprising a diagnosis or diagnostic recommendation. In some embodiments, the medical images are from a CT scan, a PET/CT scan, a SPECT scan, an MRI, an ultrasound, an X-ray, a mammogram, an angiogram, a fluorogram, a microgram, or a combination thereof. In some embodiments, the method further comprises performing, by the computer, image preprocessing comprising normalization of the plurality of medical images. In some embodiments, the normalization comprises normalization of image format, image slice spacing, image intensity, image contract, and image orientation. In some embodiments, the images are normalized to DICOM format, NIfTI format, or raw binary format. In some embodiments, the region of interest is an organ, a part of an organ, or a tissue. In some embodiments, the candidate locations comprise less than 10% of the locations in the 2D slices of the segmented medical images. In some embodiments, the first convolutional neural network has 2-20 convolutional layers and 1-10 fully connected layers. In some embodiments, the first convolutional neural network has 3-8 convolutional layers and 3-5 fully connected layers. In some embodiments, the sliding window is a window of less than 100 pixels by less than 100 pixels. In further embodiments, the sliding window is a window of 10-40 pixels by 10-40 pixels. In some embodiments, the sliding window is a window of about 31 pixels by about 31 pixels. In some embodiments, the sliding window is a window of about 16 pixels by about 16 pixels. In some embodiments, the first convolutional neural network comprises at least one neural network instance selected randomly from a plurality of neural network instances. In some embodiments, the second convolutional neural network has five or more convolutional and fully connected layers. In some embodiments, the 3D volumes are less than 100 voxels in each direction. In some embodiments, the 3D volumes are 10-40 voxels in each direction. In some embodiments, the 3D volumes are about 32 voxels in each direction. In some embodiments, the 3D volumes are about 16 voxels in each direction. In some embodiments, the second convolutional neural network selects a plurality of random locations within each volume. In some embodiments, the second convolutional neural network selects a plurality of random scales at each location. In some embodiments, the second convolutional neural network selects a plurality of random viewing angles for each location. In some embodiments, the second convolutional neural network comprises at least one neural network instance selected randomly from a plurality of neural network instances. In some embodiments, the method further comprises performing, by the computer, post-processing of the refined locations. In some embodiments, the post-processing comprises characterizing one or more of: centroid location, volume, shape, intensity, density, transparency, and regularity. In some embodiments, the post-processing comprises determination whether two or more refined locations are parts of the same disease site. In some embodiments, the method is performed in real-time or near real-time and generates a real-time or near real-time diagnosis or diagnostic recommendation. In some embodiments, the diagnosis or diagnostic recommendation comprises a determination whether any locations are disease sites. In some embodiments, the report comprises an informational overlay on one or more of the medical images. In some embodiments, the overlay comprises a point location indictor, an area indicator, or a contour indicator. In some embodiments, the report comprises one or more medical images color-coded to indicate disease type. In some embodiments, the report comprises one or more medical images heat mapped to indicate diagnostic confidence level. In some embodiments, the report comprises a time course generated by applying the application to medical images captured at two or more time points. In some embodiments, the method further comprises training the first and second convolutional neural networks to identify critical clinical signs of a disease. In some embodiments, the first and second convolutional neural networks are trained using medical images labeled by a human expert and subjected to preprocessing to normalize image format, image slice spacing, image intensity, image contract, and image orientation. In some embodiments, the first and second convolutional neural networks are trained using medical images balanced for normal and disease locations.

DETAILED DESCRIPTION OF THE INVENTION

Figure 1:
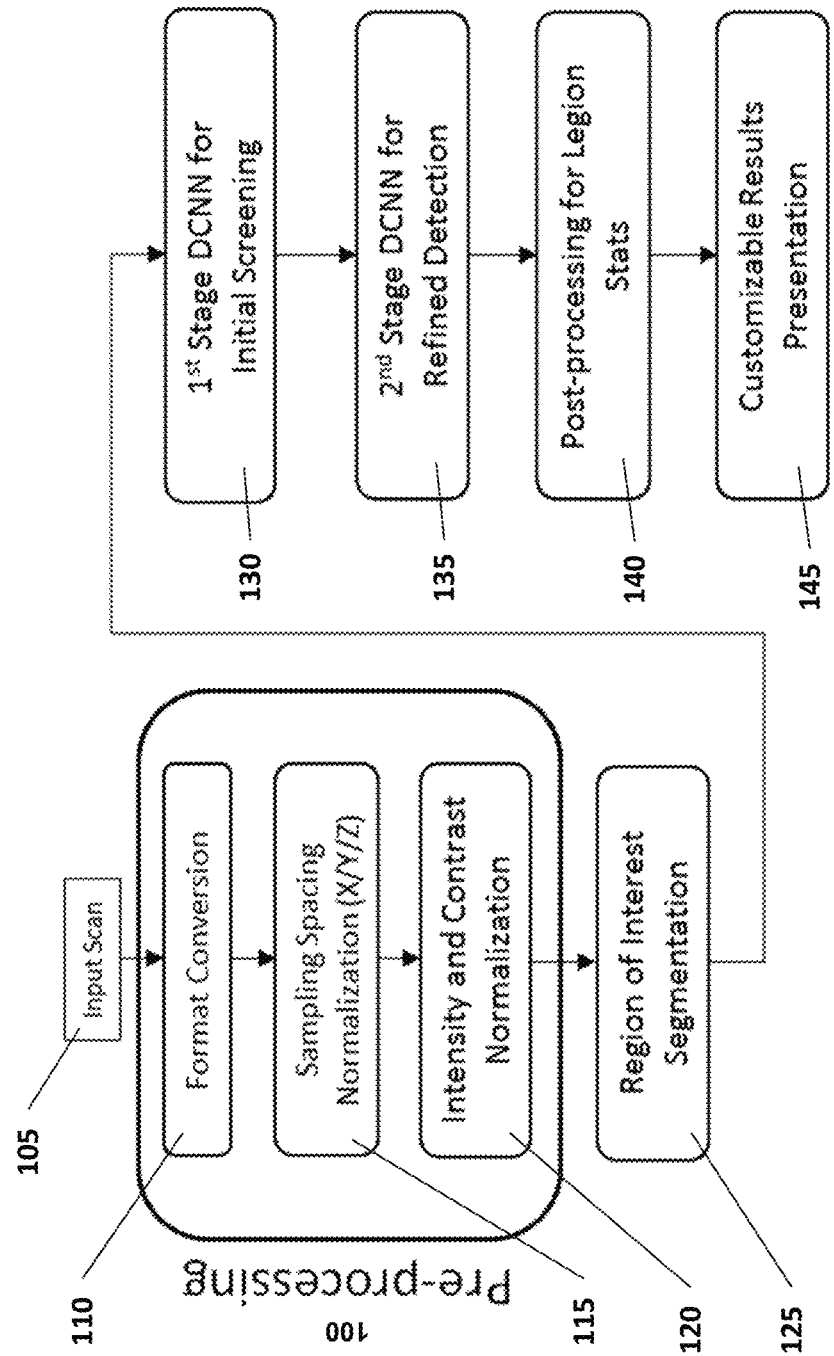
FIG. 1 shows a non-limiting example of a process flow diagram; in this case, a diagram illustrating an overall process for applying deep convolutional neural networks to medical images to generate a real-time or near real-time diagnosis.

Existing CAD systems rely on manually crafted features to describe unhealthy tissues. However, manual work involves a lot of domain knowledge to the specific problem, although mostly it is still very heuristic. Once a feature is considered, it is hard to adapt to new data and cases. As a result, the system often suffers from low detection rate and high false positive, and cannot meet the requirements of clinical use. The technologies disclosed herein employ artificial intelligence algorithms to automatically analyze medical images to identify disease features. The identified features are then used for disease diagnosis with high accuracy.

On the other hand, existing CAD systems face slow processing time. Medical imaging generates a large volume of image data, whose processing and analysis usually take long time. In some applications, the processing is too complex to be performed in real-time. The technologies disclosed herein include a real-time automatic image analysis. To create a faster processing, the technologies disclosed herein start with segmenting a region of interest, and the following processing is applied to the region rather than to the entire image domain. Further, an initial screening is performed on individual 2D slices rather on the 3D volumetric space, in order to conserve computational resources. Next, a refined detection step is applied on the initial screening results. The segmentation and the cascaded process allow fast processing, and achieve real-time or near real-time results. On the other hand, to achieve high accuracy, the disclosed technologies utilize convolutional neural networks with randomized optimization. The disclosed technologies include deep learning-based solution, such as deep (multi-layer) convolutional neural networks (DCNN), to automatically learn critical features and their characteristics about a disease, by scanning through large amounts of expert-labeled medical images. The automatically learned features are more discriminative than manually selected features, and can more easily adapt to new data/cases.

Described herein, in certain embodiments is a computer-implemented system comprising: a digital processing device comprising: at least one processor, an operating system configured to perform executable instructions, a memory, and a computer program including instructions executable by the digital processing device to create an application applying deep convolutional neural networks to medical images to generate a real-time or near real-time diagnosis or diagnostic recommendation, the application comprising: (a) a software module performing image segmentation of a plurality of medical images, the image segmentation comprising isolating a region of interest from each image; (b) a software module applying a cascaded deep convolutional neural network detection structure to the segmented images, the detection structure comprising: (1) a first stage employing a first convolutional neural network to screen all possible locations in each 2D slice of the segmented medical images by a sliding window methodology to identify one or more candidate locations; and (2) a second stage employing a second convolutional neural network to screen 3D volumes constructed from the candidate locations by selecting at least one random location within each volume with a random scale and a random viewing angle to identify one or more refined locations and classifying the refined locations; and (b) a software module automatically generating a report comprising a diagnosis or diagnostic recommendation. In some embodiments, the medical images are from a CT scan, a PET/CT scan, a SPECT scan, an MRI, an ultrasound, an X-ray, a mammogram, an angiogram, a fluorogram, a microgram, or a combination thereof. In some embodiments, the application further comprises a software module performing image preprocessing comprising normalization of the plurality of medical images. In some embodiments, the normalization comprises normalization of image format, image slice spacing, image intensity, image contract, and image orientation. In some embodiments, the images are normalized to DICOM format, NIfTI format, or raw binary format. In some embodiments, the region of interest is an organ, a part of an organ, or a tissue. In some embodiments, the candidate locations comprise less than 10% of the locations in the 2D slices of the segmented medical images. In some embodiments, the first convolutional neural network has 2-20 convolutional layers and 1-10 fully connected layers. In some embodiments, the first convolutional neural network has 3-8 convolutional layers and 3-5 fully connected layers. In some embodiments, the sliding window is a window of less than 100 pixels by less than 100 pixels. In some embodiments, the sliding window is a window of 10-40 pixels by 10-40 pixels. In some embodiments, the sliding window is a window of about 31 pixels by about 31 pixels. In some embodiments, the sliding window is a window of about 16 pixels by about 16 pixels. In some embodiments, the first convolutional neural network comprises at least one neural network instance selected randomly from a plurality of neural network instances. In some embodiments, the second convolutional neural network has five or more convolutional and fully connected layers. In some embodiments, the 3D volumes are less than 100 voxels in each direction. In further embodiments, the 3D volumes are 10-40 voxels in each direction. In still further embodiments, the 3D volumes are about 32 voxels in each direction. In some embodiments, the 3D volumes are about 16 voxels in each direction. In some embodiments, the second convolutional neural network selects a plurality of random locations within each volume. In some embodiments, the second convolutional neural network selects a plurality of random scales at each location. In some embodiments, the second convolutional neural network selects a plurality of random viewing angles for each location. In some embodiments, the second convolutional neural network comprises at least one neural network instance selected randomly from a plurality of neural network instances. In some embodiments, the application further comprises a software module performing post-processing of the refined locations. In further embodiments, the post-processing comprises characterizing one or more of: centroid location, volume, shape, intensity, density, transparency, and regularity. In still further embodiments, the post-processing comprises determination whether two or more refined locations are parts of the same disease site. In some embodiments, wherein the application runs in real-time or near real-time and generates a real-time or near real-time diagnosis or diagnostic recommendation. In some embodiments, the diagnosis or diagnostic recommendation comprises a determination whether any locations are disease sites. In some embodiments, the report comprises an informational overlay on one or more of the medical images. In further embodiments, the overlay comprises a point location indictor, an area indicator, or a contour indicator. In some embodiments, the report comprises one or more medical images color-coded to indicate disease type. In some embodiments, the report comprises one or more medical images heat mapped to indicate diagnostic confidence level. In some embodiments, the report comprises a time course generated by applying the application to medical images captured at two or more time points. In some embodiments, the first and second convolutional neural networks are trained to identify critical clinical signs of a disease. In further embodiments, the first and second convolutional neural networks are trained using medical images labeled by a human expert and subjected to preprocessing to normalize image format, image slice spacing, image intensity, image contract, and image orientation. In some embodiments, the first and second convolutional neural networks are trained using medical images balanced for normal and disease locations.

Also described herein, in certain embodiments are non-transitory computer-readable storage media encoded with a computer program including instructions executable by a processor to create an application applying deep convolutional neural networks to medical images to generate a real-time or near real-time diagnosis or diagnostic recommendation, the application comprising: (a) a software module performing image segmentation of a plurality of medical images, the image segmentation comprising isolating a region of interest from each image; (b) a software module applying a cascaded deep convolutional neural network detection structure to the segmented images, the detection structure comprising: (1) a first stage employing a first convolutional neural network to screen all possible locations in each 2D slice of the segmented medical images by a sliding window methodology to identify one or more candidate locations; and (2) a second stage employing a second convolutional neural network to screen 3D volumes constructed from the candidate locations by selecting at least one random location within each volume with a random scale and a random viewing angle to identify one or more refined locations and classifying the refined locations; and (c) a software module automatically generating a report comprising a diagnosis or diagnostic recommendation. In some embodiments, the medical images are from a CT scan, a PET/CT scan, a SPECT scan, an MM, an ultrasound, an X-ray, a mammogram, an angiogram, a fluorogram, a microgram, or a combination thereof. In some embodiments, the application further comprises a software module performing image preprocessing comprising normalization of the plurality of medical images. In some embodiments, the normalization comprises normalization of image format, image slice spacing, image intensity, image contract, and image orientation. In some embodiments, the images are normalized to DICOM format, NIfTI format, or raw binary format. In some embodiments, the region of interest is an organ, a part of an organ, or a tissue. In some embodiments, the candidate locations comprise less than 10% of the locations in the 2D slices of the segmented medical images. In some embodiments, the first convolutional neural network has 2-20 convolutional layers and 1-10 fully connected layers. In some embodiments, the first convolutional neural network has 3-8 convolutional layers and 3-5 fully connected layers. In some embodiments, the sliding window is a window of less than 100 pixels by less than 100 pixels. In some embodiments, the sliding window is a window of 10-40 pixels by 10-40 pixels. In further embodiments, the sliding window is a window of about 31 pixels by about 31 pixels. In further embodiments, the sliding window is a window of about 16 pixels by about 16 pixels. In some embodiments, the first convolutional neural network comprises at least one neural network instance selected randomly from a plurality of neural network instances. In some embodiments, the second convolutional neural network has five or more convolutional and fully connected layers. In some embodiments, the 3D volumes are less than 100 voxels in each direction. In some embodiments, the 3D volumes are 10-40 voxels in each direction. In some embodiments, the 3D volumes are about 32 voxels in each direction. In some embodiments, the 3D volumes are about 16 voxels in each direction. In some embodiments, the second convolutional neural network selects a plurality of random locations within each volume. In some embodiments, the second convolutional neural network selects a plurality of random scales at each location. In some embodiments, the second convolutional neural network selects a plurality of random viewing angles for each location. In some embodiments, the second convolutional neural network comprises at least one neural network instance selected randomly from a plurality of neural network instances. In some embodiments, the application further comprises a software module performing post-processing of the refined locations. In some embodiments, the post-processing comprises characterizing one or more of: centroid location, volume, shape, intensity, density, transparency, and regularity. In some embodiments, the post-processing comprises determination whether two or more refined locations are parts of the same disease site. In some embodiments, the application runs in real-time or near real-time and generates a real-time or near real-time diagnosis or diagnostic recommendation. In some embodiments, the diagnosis or diagnostic recommendation comprises a determination whether any locations are disease sites. In some embodiments, the report comprises an informational overlay on one or more of the medical images. In some embodiments, the overlay comprises a point location indictor, an area indicator, or a contour indicator. In some embodiments, the report comprises one or more medical images color-coded to indicate disease type. In some embodiments, the report comprises one or more medical images heat mapped to indicate diagnostic confidence level. In some embodiments, the report comprises a time course generated by applying the application to medical images captured at two or more time points. In some embodiments, the first and second convolutional neural networks are trained to identify critical clinical signs of a disease. In some embodiments, the first and second convolutional neural networks are trained using medical images labeled by a human expert and subjected to preprocessing to normalize image format, image slice spacing, image intensity, image contract, and image orientation. In some embodiments, the first and second convolutional neural networks are trained using medical images balanced for normal and disease locations.

Also described herein, in certain embodiments is a computer-implemented method of applying deep convolutional neural networks to medical images to generate a real-time or near real-time diagnosis or diagnostic recommendation comprising: (a) performing, by a computer, image segmentation of a plurality of medical images, the image segmentation comprising isolating a region of interest from each image; (b) applying, by the computer, a cascaded deep convolutional neural network detection structure to the segmented images, the detection structure comprising: (1) a first stage employing a first convolutional neural network to screen all possible locations in each 2D slice of the segmented medical images by a sliding window methodology to identify one or more candidate locations; and (2) a second stage employing a second convolutional neural network to screen 3D volumes constructed from the candidate locations by selecting at least one random location within each volume with a random scale and a random viewing angle to identify one or more refined locations and classifying the refined locations; and (c) automatically generating, by the computer, a report comprising a diagnosis or diagnostic recommendation. In some embodiments, the medical images are from a CT scan, a PET/CT scan, a SPECT scan, an MM, an ultrasound, an X-ray, a mammogram, an angiogram, a fluorogram, a microgram, or a combination thereof. In some embodiments, the method further comprises performing, by the computer, image preprocessing comprising normalization of the plurality of medical images. In some embodiments, the normalization comprises normalization of image format, image slice spacing, image intensity, image contract, and image orientation. In some embodiments, the images are normalized to DICOM format, NIfTI format, or raw binary format. In some embodiments, the region of interest is an organ, a part of an organ, or a tissue. In some embodiments, the candidate locations comprise less than 10% of the locations in the 2D slices of the segmented medical images. In some embodiments, the first convolutional neural network has 2-20 convolutional layers and 1-10 fully connected layers. In some embodiments, the first convolutional neural network has 3-8 convolutional layers and 3-5 fully connected layers. In some embodiments, the sliding window is a window of less than 100 pixels by less than 100 pixels. In further embodiments, the sliding window is a window of 10-40 pixels by 10-40 pixels. In some embodiments, the sliding window is a window of about 31 pixels by about 31 pixels. In some embodiments, the sliding window is a window of about 16 pixels by about 16 pixels. In some embodiments, the first convolutional neural network comprises at least one neural network instance selected randomly from a plurality of neural network instances. In some embodiments, the second convolutional neural network has five or more convolutional and fully connected layers. In some embodiments, the 3D volumes are less than 100 voxels in each direction. In some embodiments, the 3D volumes are 10-40 voxels in each direction. In some embodiments, the 3D volumes are about 32 voxels in each direction. In some embodiments, the 3D volumes are about 16 voxels in each direction. In some embodiments, the second convolutional neural network selects a plurality of random locations within each volume. In some embodiments, the second convolutional neural network selects a plurality of random scales at each location. In some embodiments, the second convolutional neural network selects a plurality of random viewing angles for each location. In some embodiments, the second convolutional neural network comprises at least one neural network instance selected randomly from a plurality of neural network instances. In some embodiments, the method further comprises performing, by the computer, post-processing of the refined locations. In some embodiments, the post-processing comprises characterizing one or more of: centroid location, volume, shape, intensity, density, transparency, and regularity. In some embodiments, the post-processing comprises determination whether two or more refined locations are parts of the same disease site. In some embodiments, the method is performed in real-time or near real-time and generates a real-time or near real-time diagnosis or diagnostic recommendation. In some embodiments, the diagnosis or diagnostic recommendation comprises a determination whether any locations are disease sites. In some embodiments, the report comprises an informational overlay on one or more of the medical images. In some embodiments, the overlay comprises a point location indictor, an area indicator, or a contour indicator. In some embodiments, the report comprises one or more medical images color-coded to indicate disease type. In some embodiments, the report comprises one or more medical images heat mapped to indicate diagnostic confidence level. In some embodiments, the report comprises a time course generated by applying the application to medical images captured at two or more time points. In some embodiments, the method further comprises training the first and second convolutional neural networks to identify critical clinical signs of a disease. In some embodiments, the first and second convolutional neural networks are trained using medical images labeled by a human expert and subjected to preprocessing to normalize image format, image slice spacing, image intensity, image contract, and image orientation. In some embodiments, the first and second convolutional neural networks are trained using medical images balanced for normal and disease locations.

CERTAIN DEFINITIONS

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated.

Medical Images

In various embodiments, the platforms, systems, media, and methods described herein include a medical image. Referring FIG. 1, a medical imaging machine scans a subject and generates input scans 105 to the system. Examples of scans include, but not limited to, a CT scan, a SPECT scan, an MRI, an X-ray, an ultrasound, an endoscopy, a colonoscopy, a mammogram, an angiogram, a fluorogram, a microgram, or a combination thereof.

Image Pre-Processing

In various embodiments, the platforms, systems, media, and methods described herein include image pre-processing. Referring again to FIG. 1, the system further performs a pre-processing step 100. In some embodiments, the pre-processing 100 comprises format conversion 110. In some embodiments, the pre-processing 100 comprises normalization of the plurality of medical images. In some embodiments, the normalization comprises normalizing sampling space (115) in x-axis, y-axis, and z-axis. In some embodiments, the normalization comprises normalization of image format, image slice spacing, image intensity, image contract, and image orientation. In some embodiments, the normalization comprises normalizing images into a DICOM or NIfTI format. In some embodiments, the pre-processing 100 comprises intensity and contrast normalization 120.

Image Segmentation

Referring again to FIG. 1, when pre-processing 100 is complete, a segmentation 125 on a region of interest is performed. In further embodiments, a region of interest is an organ, a chamber, a tissue structure, a component of an organ, or a part of an organ. In still further embodiments, segmented images are processed under the first stage DCNN for initial screening 130. In still further embodiments, the segmented images are processed under the second stage DCNN for refined detection 135. Analysis results of DCNN are under post-processing for statistical analysis 140, for example lung nodule identification. A final step 145 comprises customizable results presentation.

In some embodiments, a region of interest comprises candidate locations for further analysis. In some embodiments, candidate locations comprise less than 5%, 10%, 15%, 20%, 25%, 30%, 35%, or 40%, including increments therein, of the locations in the 2D slices of the segmented medical images.

Cascaded Deep Convolutional Neural Network Detection Structure

In various embodiments, the platforms, systems, media, and methods described herein include a cascaded deep convolution neural network (DCNN) detection structure, or use of the same. In some embodiments, the detection structure comprises two or more deep convolution neural networks in two stages. Referring again to FIG. 1, a cascaded DCNN detection structure includes a first stage DCNN for initial screening 130 and a second stage DCNN for refined detection 135.

Figure 2:
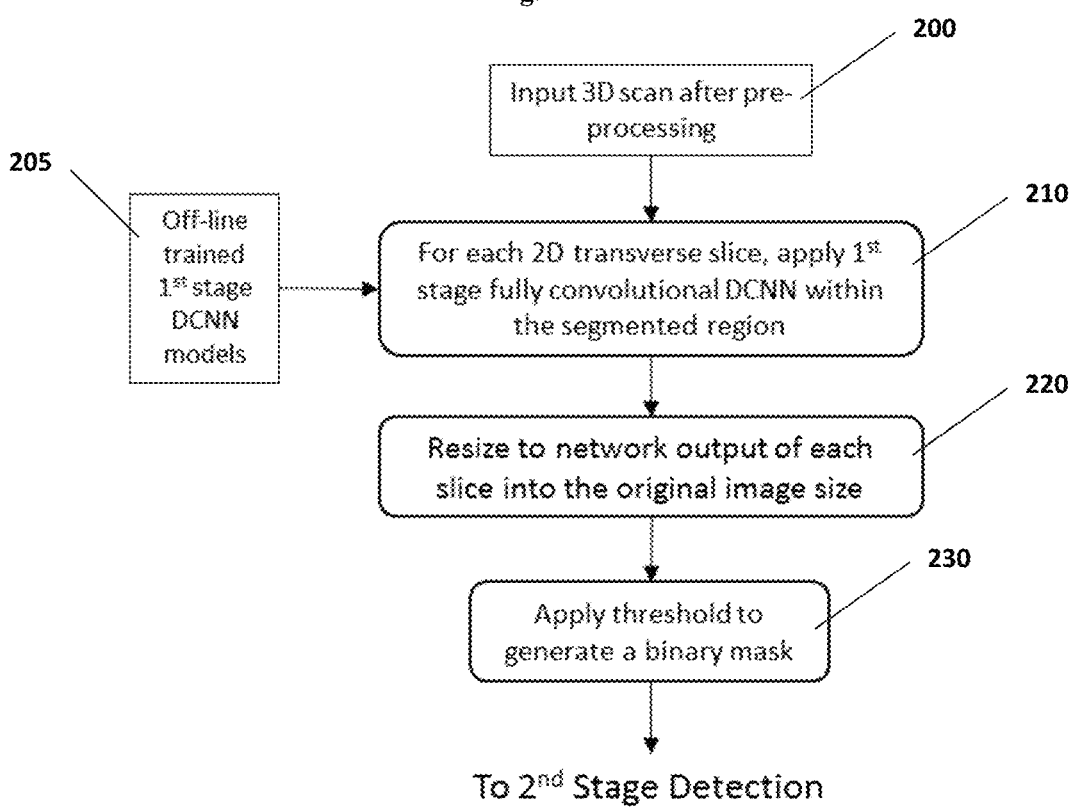
FIG. 2 shows a non-limiting example of a process flow diagram; in this case, a diagram illustrating an initial screening process for applying deep convolutional neural networks to medical images to generate a real-time or near real-time diagnosis.

Referring to FIG. 2, a first stage starts with a step 200 taking medical images of a 3D scan after pre-processing. On the other hand, one or more off-line trained DCNN models 205 are fed into the analysis. The step 210 uses the DCNN models to process segmented regions on individual 2D transversal slices. In some embodiments, the DCNN is applied based on a sliding window methodology. In various further embodiments, the sliding window comprises a window of less than 10 pixels by less than 10 pixels, less than 20 pixels by less than 20 pixels, less than 30 pixels by less than 30 pixels, less than 50 pixels by less than 50 pixels, less than 100 pixels by less than 100 pixels, or less than 200 pixels by less than 200 pixels, including increments therein. In a particular embodiment, the sliding window is a window of about 31 pixels by about 31 pixels. In this particular embodiment, the DCNN has three convolutional layers and two fully connected layers. Further in this embodiment, step 220 resizes the network output of each slice into the original image size. In still further embodiments, step 230 applies a threshold to generate a binary mask to identify candidate locations of diagnostic features. In some cases, the candidate locations comprise less than 10% of the locations in the 2D slices of the segmented medical images. In some embodiments, the threshold in step 230 is selected based on a receiver operating characteristic (ROC) analysis of the first stage DCNN. In various further embodiments, the threshold is selected such that the candidate locations comprise more than about 90%, more than about 91%, more than about 92%, more than about 93%, more than about 94%, more than about 95%, more than about 96%, more than about 97%, more than about 98%, or more than about 99% of the lesion locations in the training set. In a particular embodiment, the threshold is selected such that the candidate locations comprise more than about 95% of the lesion locations in the training set. Finally, the binary mask is propagated to a second stage detection.

In some embodiments, a second stage analysis employs a second DCNN to screen 3D volumes constructed from the candidate locations by selecting at least one random location within each volume with a random scale and a random viewing angle to identify one or more refined locations and classifying the refined locations. In some embodiments, the 3D volumes are less than 50 voxels, 100 voxels, 200 voxels, or 300 voxels in each direction, including increments therein. In particular embodiments, the 3D volumes are about 8, 16, 32, 48, or 64 voxels in each direction, including increments therein. In some embodiments, the second DCNN selects a plurality of random locations within each volume. In some embodiments, the second DCNN selects a plurality of random scales at each location. In some embodiments, the second DCNN selects a plurality of random viewing angles for each location.

In some embodiments, the convolutional neural network in the first stage comprises 3-8 convolutional layers and 3-5 fully connected layers. In some embodiments, this first convolutional neural network comprises at least one neural network instance selected randomly from a plurality of neural network instances. The plurality of neural network instances has different parameters, or has different network structures.

Figure 3:
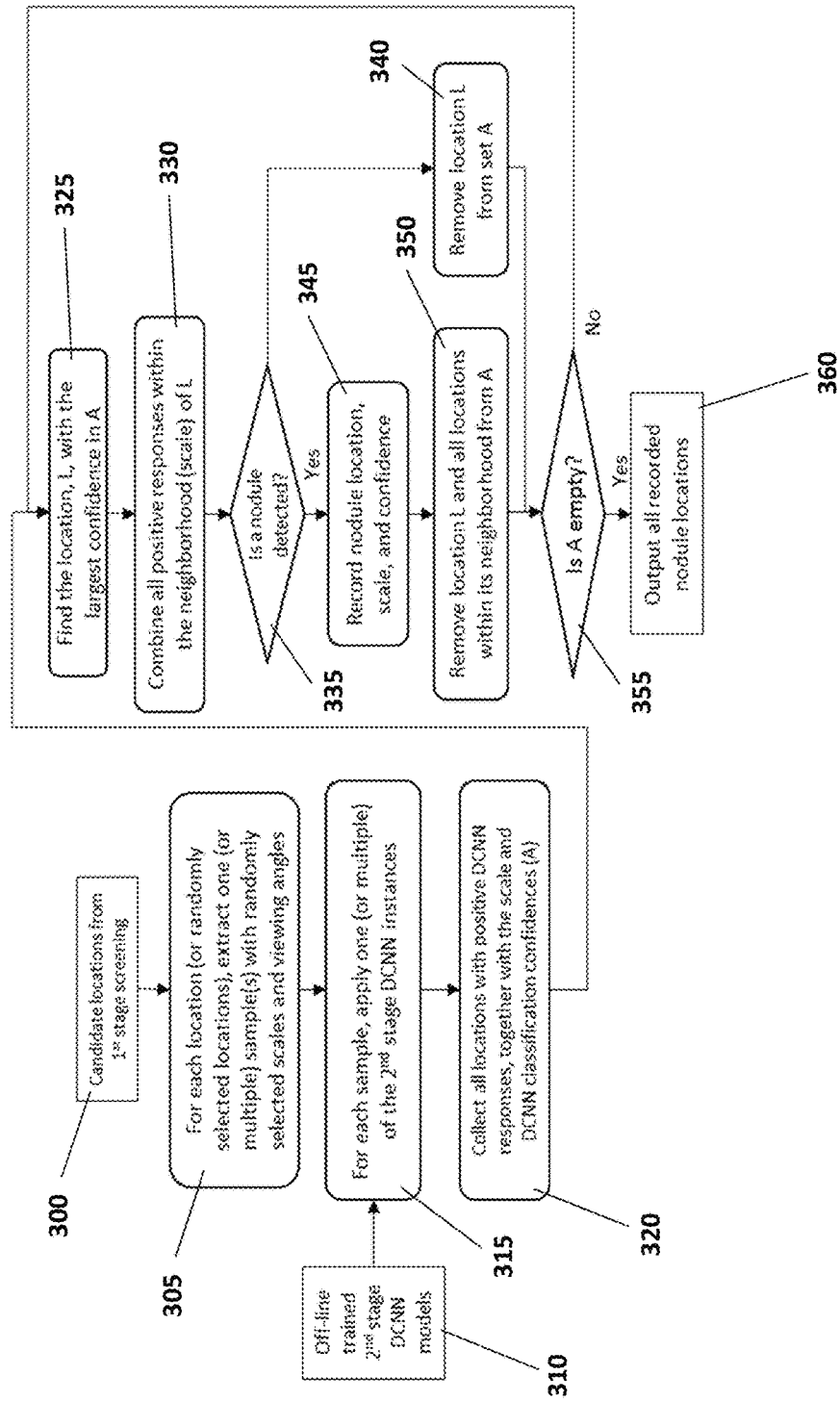
FIG. 3 shows a non-limiting example of a process flow diagram; in this case, a diagram illustrating an refined screening process for applying deep convolutional neural networks to medical images to generate a real-time or near real-time diagnosis.

Embodiments of second stage analysis are described below. Referring FIG. 3, candidate locations 300 generated from the first stage screening are fed into the second stage analysis. In step 305, for each location, the system extracts one or more samples with randomly selected scales and viewing angles. On the other hand, off-line trained second stage DCNN models 310 are fed to the analysis. In step 315, for each sample, one or more DCNN instances are applied. In some embodiments, the second DCNN has five or more convolutional and fully connected layers. In step 320, the system then collects all locations with positive DCNN responses, together with the scale and DCNN classification confidences, denoted by A. In step 325, the system finds location L with the largest confidence in A. In step 330, the system combines all positive responses within the neighborhood of the location L. Further, the step 335 determines if an abnormality (e.g., a lung nodule) is detected. If detected, step 345 records the location of abnormality and its scale and confidence, followed by step 350 where the system removes the location L and all locations within its neighborhood from the set A. If abnormality is not detected in step 335, the system removes location L from the set A. Then, the system checks if the set A is empty in step 355. If the set A is empty, the second stage is terminated and outputs all recorded locations with abnormalities 360. If the set A is not empty in step 355, the system repeats the analysis starting step 325 with another element in A.

In some embodiments, the second stage analysis is dedicated to screen 3D volumes constructed from the candidate locations by selecting at least one random location within each volume with a random scale and a random viewing angle to identify one or more refined locations and classifying the refined locations. In some embodiments, the 3D volumes comprise less than 100 voxels in each direction. In some embodiments, the 3D volumes comprise 10-40 voxels in each direction. In some embodiments, the 3D volumes comprise about 32 voxels in each direction. In some embodiments, the 3D volumes comprise about 16 voxels in each direction.

In some embodiments, the DCNN in the second stage selects a plurality of random locations within each volume. In some embodiments, the DCNN in the second stage selects a plurality of random scales at each location. In some embodiments, the DCNN in the second stage selects a plurality of random viewing angles for each location. In some embodiments, randomized algorithms are based on a probabilistic modeling; for example, the locations are based on a uniform or a normal distribution.

In some embodiments, the convolutional neural network in the second stage comprises at least 1, 2, 3, 4, 5, 6, 7, 8, 9, or 10 convolutional or fully connected layers. In some embodiments, this convolutional neural network comprises at least one neural network instance selected randomly from a plurality of neural network instances. The plurality of neural network instances has different parameters, or has different network structures.

Post-Processing and Reports

In various embodiments, the platforms, systems, media, and methods described herein include post-processing of refined locations, or use of the same. In some embodiments, the post-processing comprises characterizing one or more of: centroid location, volume, shape, intensity, density, transparency, and regularity. In some embodiments, the post-processing comprises determination whether two or more refined locations are parts of the same disease site.

In various embodiments, the platforms, systems, media, and methods described herein include a report generation, or use of the same. After automatic detection, the candidate abnormal locations (e.g., lung nodules) are presented to users for final review. Depending on the user preferences, the results can be presented in different ways.

In some embodiments, a report comprises an informational overlay on one or more of the medical images. In some embodiments, the report comprises one or more medical images color coded to indicate disease type. In some embodiments, the report comprises one or more medical images heat mapped to indicate diagnosis confidence level. In some embodiments, the report comprises a time course generated by applying the application to medical images captured at two or more time points. In further embodiments, the overlay comprises a point location indictor, an area indicator, or a contour indicator. In still further embodiments, the overlay comprises color coding for segmented regions and/or abnormal locations.

Figure 4:
FIG. 4 shows a non-limiting example of a report described herein; in this case, a report including a lung nodule analysis.

In some embodiments, a report comprises an informational text-based report. Referring to FIG. 4, a summary report of lung nodule detection is presented on top of the 2D or 3D images with detected lung nodule. In additional embodiments, the text-based report comprises measurements (e.g., sizes, volumes, lengths, widths, depths, dimensions, locations, and diameters). In additional embodiments, the text-based report comprises a confidence level, such as probability or a statistical measure.

In some embodiments, a report comprises a biomarker tracking from retrospective scans. A system registers a detected lesion in previous scan, and presents the progression of the lesion. In some embodiments, a report comprises an animated visualization.

The technologies disclosed herein segment a region of interest and the following cascaded detection structure is applied to the region of interest rather than to the entire image domain. Further, an initial screening is performed on individual 2D slices rather on the 3D volumetric space, in order to conserve computational resources. Next, a refined detection step is applied on the initial screening results. The segmentation and the cascaded detection process allow less data to be loaded in the memory, and analyzing the smaller volume of segmented data requires less CPU cycles for computations. The overall effect of consuming less memory and CPU cycles leads to fast processing, and achieves real-time or near real-time image processing and report generation. In further embodiments, the report comprises a diagnostic recommendation or a diagnosis, e.g., an indication/probability of whether any locations are disease sites.

Convolutional Neural Network Training

In some embodiments, a DCNN is trained in a training step. In some embodiments, a training step begins with pre-processing, as described above. In further embodiments, the training collects sample to perform analysis on multiple scales, multiple angles/views, multiple locations, random locations. In addition, a training step comprises balancing data for different classes.

In some embodiments, the first and second convolutional neural networks are trained to identify critical clinical signs of a disease. In some embodiments, the first and second convolutional neural networks are trained using medical images labeled by a human expert and subjected to preprocessing to normalize image format, image slice spacing, image intensity, image contract, and image orientation. In some embodiments, the first and second convolutional neural networks are trained using medical images balanced for normal and disease locations.

In some embodiments, a DCNN design and training includes consideration in learning rate and/or iterations. In some embodiments, a training step comprises considerations performance (e.g., ROC analysis) or operating point selection.

Digital Processing Device

In some embodiments, the platforms, systems, media, and methods described herein include a digital processing device, or use of the same. In further embodiments, the digital processing device includes one or more hardware central processing units (CPUs) or general purpose graphics processing units (GPGPUs) that carry out the device's functions. In still further embodiments, the digital processing device further comprises an operating system configured to perform executable instructions. In some embodiments, the digital processing device is optionally connected a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, handheld computers, and tablet computers. Suitable tablet computers include those with booklet, slate, and convertible configurations, known to those of skill in the art.

In some embodiments, the digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes, optical disk drives, and cloud computing based storage. In further embodiments, the storage and/or memory device is a combination of devices such as those disclosed herein.

In some embodiments, the digital processing device includes a display to send visual information to a user. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In still further embodiments, the display is a combination of devices such as those disclosed herein.

In some embodiments, the digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera or other sensor to capture motion or visual input. In still further embodiments, the input device is a combination of devices such as those disclosed herein.

In various embodiments, the platforms, systems, media, and methods described herein include a cloud computing environment. In some embodiments, a cloud computing environment comprises a plurality of computing processors. The cloud computing environment is located in one or more geolocations. The cloud computing environment is coupled with a medical scanner via a network. In some embodiments, a scanner generates a set of images and transmits the images to the cloud computing environment. The transmission of the images can be in a serial mode or in a batch mode. Once the cloud computing environment receives one or more images, the system performs segmentation, cascaded detection, report generation, and the like.

Figure 7:
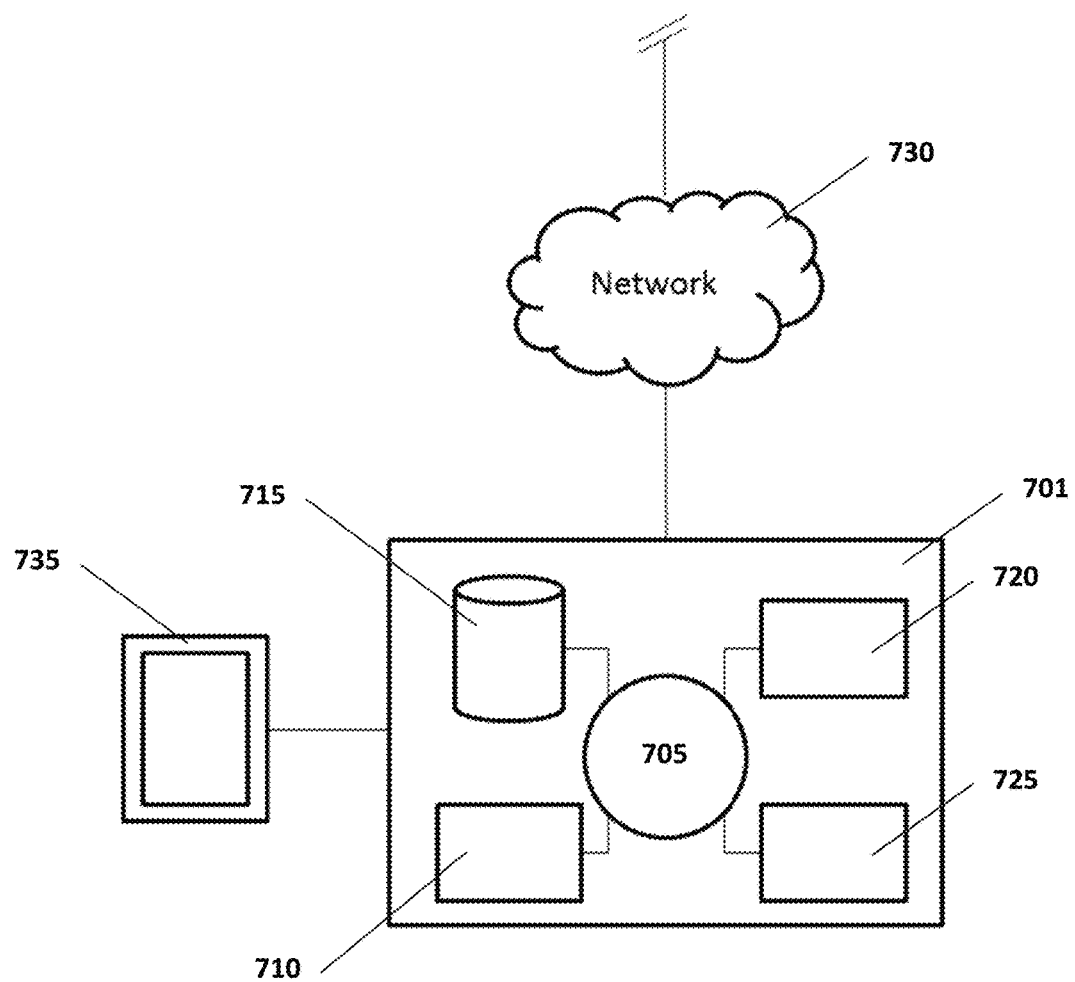
FIG. 7 shows a non-limiting example of a digital processing device; in this case, a device with one or more CPUs, a memory, a communication interface, and a display.

Referring to FIG. 7, in a particular embodiment, an exemplary digital processing device 701 is programmed or otherwise configured to perform image processing. The device 701 can regulate various aspects of image processing of the present disclosure, such as, for example, segmentation, detection, DCNN, report generation, and training. In this embodiment, the digital processing device 701 includes a central processing unit (CPU, also "processor" and "computer processor" herein) 705, which can be a single core or multi-core processor, or a plurality of processors for parallel processing. As described herein, a graphics processing unit (GPU), which facilitates parallel processing, is also suitable. The digital processing device 701 also includes memory or memory location 710 (e.g., random-access memory, read-only memory, flash memory), electronic storage unit 715 (e.g., hard disk), communication interface 720 (e.g., network adapter) for communicating with one or more other systems, and peripheral devices 725, such as cache, other memory, data storage and/or electronic display adapters. The memory 710, storage unit 715, interface 720 and peripheral devices 725 are in communication with the CPU 705 through a communication bus (solid lines), such as a motherboard. The storage unit 715 can be a data storage unit (or data repository) for storing data. The digital processing device 701 can be operatively coupled to a computer network ("network") 730 with the aid of the communication interface 720. The network 730 can be the Internet, an internet and/or extranet, or an intranet and/or extranet that is in communication with the Internet. The network 730 in some cases is a telecommunication and/or data network. The network 730 can include one or more computer servers, which can enable distributed computing, such as cloud computing. The network 730, in some cases with the aid of the device 701, can implement a peer-to-peer network, which may enable devices coupled to the device 701 to behave as a client or a server.

Continuing to refer to FIG. 7, the CPU 705 can execute a sequence of machine-readable instructions, which can be embodied in a program or software. The instructions may be stored in a memory location, such as the memory 710. The instructions can be directed to the CPU 705, which can subsequently program or otherwise configure the CPU 705 to implement methods of the present disclosure. Examples of operations performed by the CPU 705 can include fetch, decode, execute, and write back. The CPU 705 can be part of a circuit, such as an integrated circuit. One or more other components of the device 701 can be included in the circuit. In some cases, the circuit is an application specific integrated circuit (ASIC) or a field programmable gate array (FPGA).

Continuing to refer to FIG. 7, the storage unit 715 can store files, such as drivers, libraries and saved programs. The storage unit 715 can store user data, e.g., user preferences and user programs. The digital processing device 701 in some cases can include one or more additional data storage units that are external, such as located on a remote server that is in communication through an intranet or the Internet.

Continuing to refer to FIG. 7, the digital processing device 701 can communicate with one or more remote computer systems through the network 730. For instance, the device 701 can communicate with a remote computer system 735 of a user. Examples of remote computer systems include personal computers (e.g., portable PC), slate or tablet PCs (e.g., Apple® iPad, Samsung® Galaxy Tab), telephones, Smart phones (e.g., Apple® iPhone, Android-enabled device, Blackberry®), or personal digital assistants.

Methods as described herein can be implemented by way of machine (e.g., computer processor) executable code stored on an electronic storage location of the digital processing device 101, such as, for example, on the memory 710 or electronic storage unit 715. The machine executable or machine readable code can be provided in the form of software. During use, the code can be executed by the processor 705. In some cases, the code can be retrieved from the storage unit 715 and stored on the memory 710 for ready access by the processor 705. In some situations, the electronic storage unit 715 can be precluded, and machine-executable instructions are stored on memory 710.

Non-Transitory Computer Readable Storage Medium

In some embodiments, the platforms, systems, media, and methods disclosed herein include one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Computer Program

In some embodiments, the platforms, systems, media, and methods disclosed herein include at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more standalone applications, one or more web browser plug-ins, extensions, add-ins, or add-ons, or combinations thereof.

Web Application

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft® NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, MySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® ActionScript, Javascript, or Silverlight®. In some embodiments, a web application is written to some extent in a server-side coding language such as Active Server Pages (ASP), ColdFusion®, Perl, Java™, Java Server Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™, and Unity®.

Standalone Application

In some embodiments, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB .NET, or combinations thereof. Compilation is often performed, at least in part, to create an executable program. In some embodiments, a computer program includes one or more executable complied applications.

Software Modules

In some embodiments, the platforms, systems, media, and methods disclosed herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

Databases

In some embodiments, the platforms, systems, media, and methods disclosed herein include one or more databases, or use of the same. In view of the disclosure provided herein, those of skill in the art will recognize that many databases are suitable for storage and retrieval of individual (e.g., patient), medical image, and neural network/training information. In various embodiments, suitable databases include, by way of non-limiting examples, relational databases, non-relational databases, object oriented databases, object databases, entity-relationship model databases, associative databases, and XML databases. Further non-limiting examples include SQL, PostgreSQL, MySQL, Oracle, DB2, and Sybase. In some embodiments, a database is internet-based. In further embodiments, a database is web-based. In still further embodiments, a database is cloud computing-based. In other embodiments, a database is based on one or more local computer storage devices.

EXAMPLES

The following illustrative examples are representative of embodiments of the software applications, systems, and methods described herein and are not meant to be limiting in any way.

Example 1

Generation of Reports

FIG. 4 shows an example of an analysis report. The system identified location of the nodule was at upper right lung. The nodule was determined non-solid and ground glass. The centroid of the nodule was at x-y-z coordinate of 195-280-43. The nodule diameter along the long axis was 11 mm and along the short axis was 7 mm. The border shape of the nodule was irregular. The probability of being malignant was 84%.

Figure 5:
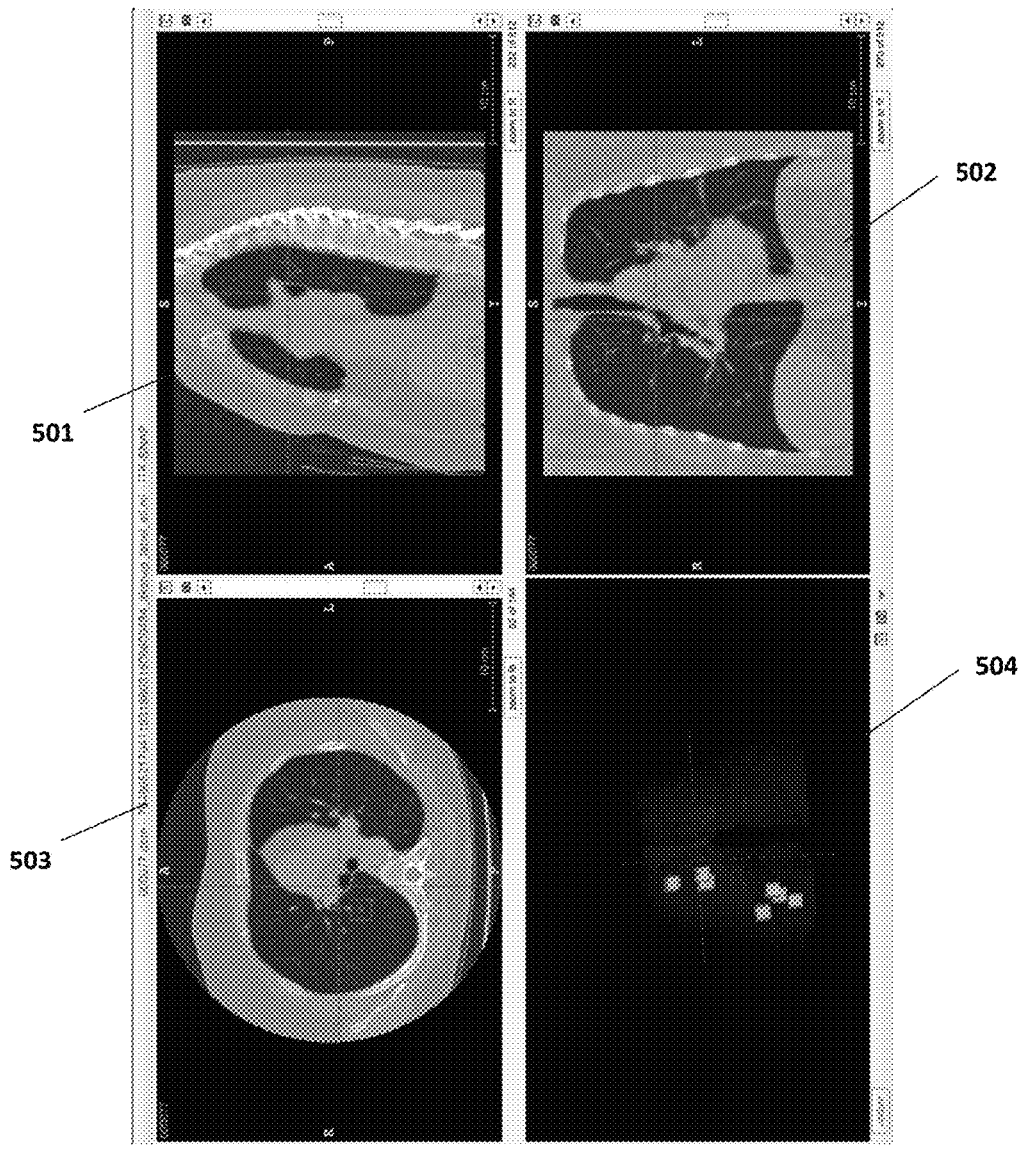
FIG. 5 shows a non-limiting example of a report described herein; in this case, a report including images of detected lung nodules.

FIG. 5 shows an example of a diagnostic report. In this example, the report comprises a user interface. Three projected views 501, 502, and 503 of a lung CT scan were presented to the user. The views 501, 502, and 503 comprised a cursor to allow the user pinpoint a location. The window 504 showed a 3D model of the segmented lung and detected nodule candidates (square dots). The 3D models were overlaid in the projected views 501, 502, and 503.

Example 2

Validation of Lung Nodule Detection

The technologies disclosed herein were applied to a publically available lung nodule dataset (LIDC-IDRI) provided by National Institute of Health (NIH). The dataset consists of 1018 CT lung scans from 1012 patients. The scans were captured using a variety of CT machines and a diverse set of parameter settings. Each voxel inside a scan had been carefully annotated by four radiologists as normal (non-nodule) or abnormal (nodule). In a training step, a five-fold cross validation was employed for the evaluation. All scans were first divided into five sets, each of which contained about the same number of scans. Each scan was randomly assigned to one of the five sets. Each evaluation iteration used four of the five sets to train the lung nodule detector, and the remaining set was used for evaluating the trained detector. In a training iteration, segmentation and cascaded detection were applied to the datasets. The evaluation is repeated five times so that each of the five sets was used as a test set.

For each evaluation, the following two metrics were used to measure the detection accuracy: Sensitivity (or Detection Rate): the percentage of labelled nodules that were successfully detected; Selectivity (or False Positive per Detected Nodule): the number of false detected candidate nodules per detected true nodule. The detection accuracies from all 5 rounds of evaluations were averaged to produce the overall detection accuracy on the entire dataset.

Figure 6:
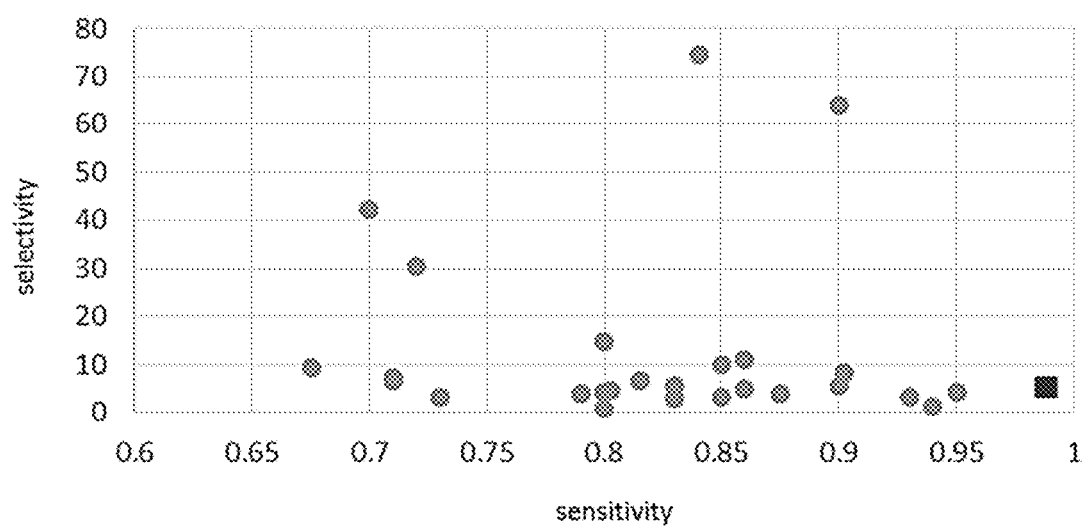
FIG. 6 shows a non-limiting example of a data graph; in this case, a graph illustrating performance of the technology described herein compared to current technologies.

Referring again FIG. 6, the overall detection accuracy based on the technologies disclosed herein is plotted as the square dot in the plot, and the accuracies based on traditional methods are plotted as the circles. The disclosed technologies achieved a better sensitivity (nodule detection rate) of 98.5% and a selectivity (false positive per true nodule) of 4 than existing systems. The compared systems were from academic publications in the last 10 years, and their detection accuracies reported in the plot were directly cited from their original publications.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

What is claimed is:

1. A computer-implemented system comprising: a digital processing device comprising: at least one processor, an operating system configured to perform executable instructions, a memory, and a computer program including instructions executable by the digital processing device to create an application applying deep convolutional neural networks to medical images to generate a real-time or near real-time diagnosis or diagnostic recommendation, the application comprising:
   a) a software module performing image segmentation of a plurality of medical images, the image segmentation comprising isolating a region of interest from each image;
   b) a software module applying a cascaded deep convolutional neural network detection structure to the segmented images, the detection structure comprising:
      i) a first stage employing a first convolutional neural network to screen all possible locations in each 2D slice of the segmented medical images by a sliding window methodology to identify one or more candidate locations; and
      ii) a second stage employing a second convolutional neural network to screen 3D volumes constructed from the candidate locations by selecting at least one random location within each volume with a random scale and a random viewing angle to identify one or more refined locations and classifying the refined locations; and
   c) a software module automatically generating a report comprising a diagnosis or diagnostic recommendation.

2. The system of claim 1, wherein the application runs in real-time or near real-time and generates a real-time or near real-time diagnosis or diagnostic recommendation.

3. The system of claim 1, wherein the diagnosis or diagnostic recommendation comprises a determination whether any locations are disease sites.

4. The system of claim 1, wherein the medical images are from a CT scan, a PET/CT scan, a SPECT scan, an MM, an ultrasound, an X-ray, a mammogram, an angiogram, a fluorogram, a microgram, or a combination thereof.

5. The system of claim 1, wherein the application further comprises a software module performing image preprocessing comprising normalization of the plurality of medical images.

6. The system of claim 5, wherein the normalization comprises normalization of image format, image slice spacing, image intensity, image contract, and image orientation.

7. The system of claim 1, wherein the region of interest is an organ, a part of an organ, or a tissue.

8. The system of claim 1, wherein the candidate locations comprise less than 10% of the locations in the 2D slices of the segmented medical images.

9. The system of claim 1, wherein the first convolutional neural network has 2-20 convolutional layers and 1-10 fully connected layers.

10. The system of claim 1, wherein the sliding window comprises a window of less than 100 pixels by less than 100 pixels.

11. The system of claim 10, wherein the sliding window comprises a window of about 31 pixels by about 31 pixels or about 16 pixels by about 16 pixels.

12. The system of claim 1, wherein the first convolutional neural network comprises at least one neural network instance selected randomly from a plurality of neural network instances and wherein the second convolutional neural network comprises at least one neural network instance selected randomly from a plurality of neural network instances.

13. The system of claim 1, wherein the second convolutional neural network has five or more convolutional and fully connected layers.

14. The system of claim 1, wherein the 3D volumes are less than 100 voxels in each direction.

15. The system of claim 1, wherein the second convolutional neural network selects a plurality of random locations within each volume.

16. The system of claim 1, wherein the second convolutional neural network selects a plurality of random scales at each location.

17. The system of claim 1, wherein the second convolutional neural network selects a plurality of random viewing angles for each location.

18. The system of claim 1, wherein the application further comprises a software module performing post-processing of the refined locations.

19. The system of claim 18, wherein the post-processing comprises characterizing one or more of: centroid location, volume, shape, intensity, density, transparency, and regularity.

20. The system of claim 18, wherein the post-processing comprises determination whether two or more refined locations are parts of the same disease site.

21. The system of claim 1, wherein the report comprises an informational overlay on one or more of the medical images.

22. The system of claim 21, wherein the overlay comprises a point location indictor, an area indicator, or a contour indicator.

23. The system of claim 1, wherein the report comprises one or more medical images color-coded to indicate disease type.

24. The system of claim 1, wherein the report comprises one or more medical images heat mapped to indicate diagnostic confidence level.

25. The system of claim 1, wherein the report comprises a time course generated by applying the application to medical images captured at two or more time points to measure progression of a disease or growth and movement of a tumor over time.

26. The system of claim 1, wherein the first and second convolutional neural networks are trained to identify critical clinical signs of a disease.

27. The system of claim 26, wherein the first and second convolutional neural networks are trained using medical images labeled by a human expert and subjected to preprocessing to normalize image format, image slice spacing, image intensity, image contract, and image orientation.

28. The system of claim 26, wherein the first and second convolutional neural networks are trained using medical images balanced for normal and disease locations.

29. Non-transitory computer-readable storage media encoded with a computer program including instructions executable by a processor to create an application applying deep convolutional neural networks to medical images to generate a real-time or near real-time diagnosis or diagnostic recommendation, the application comprising:
   a) a software module performing image segmentation of a plurality of medical images, the image segmentation comprising isolating a region of interest from each image;
   b) a software module applying a cascaded deep convolutional neural network detection structure to the segmented images, the detection structure comprising:
      i) a first stage employing a first convolutional neural network to screen all possible locations in each 2D slice of the segmented medical images by a sliding window methodology to identify one or more candidate locations; and
      ii) a second stage employing a second convolutional neural network to screen 3D volumes constructed from the candidate locations by selecting at least one random location within each volume with a random scale and a random viewing angle to identify one or more refined locations and classifying the refined locations; and
   c) a software module automatically generating a report comprising a diagnosis or diagnostic recommendation.

30. A computer-implemented method of applying deep convolutional neural networks to medical images to generate a real-time or near real-time diagnosis or diagnostic recommendation comprising:
   a) performing, by a computer, image segmentation of a plurality of medical images, the image segmentation comprising isolating a region of interest from each image;
   b) applying, by the computer, a cascaded deep convolutional neural network detection structure to the segmented images, the detection structure comprising:
      i) a first stage employing a first convolutional neural network to screen all possible locations in each 2D slice of the segmented medical images by a sliding window methodology to identify one or more candidate locations; and
      ii) a second stage employing a second convolutional neural network to screen 3D volumes constructed from the candidate locations by selecting at least one random location within each volume with a random scale and a random viewing angle to identify one or more refined locations and classifying the refined locations; and
   c) automatically generating, by the computer, a report comprising a diagnosis or diagnostic recommendation.

* * * * *

UNITED STATES PATENT AND TRADEMARK OFFICE
CERTIFICATE OF CORRECTION

| | | |
|---|---|---|
| PATENT NO. | : 9,589,374 B1 | Page 1 of 2 |
| APPLICATION NO. | : 15/225597 | |
| DATED | : March 7, 2017 | |
| INVENTOR(S) | : Gao et al. | |

It is certified that error appears in the above-identified patent and that said Letters Patent is hereby corrected as shown below:

In the Specification

Column 2, Line 33, delete "contract" and replace with --contrast--

Column 3, Line 33, delete "contract" and replace with --contrast--

Column 3, Line 61, delete "MM" and replace with --MRI--

Column 4, Line 2, delete "contract" and replace with --contrast--

Column 5, Line 1, delete "contract" and replace with --contrast--

Column 5, Line 34, delete "contract" and replace with --contrast--

Column 6, Line 35, delete "contract" and replace with --contrast--

Column 8, Line 7, delete "contract" and replace with --contrast--

Column 9, Line 7, delete "contract" and replace with --contrast--

Column 9, Line 36, delete "MM" and replace with --MRI--

Column 9, Line 43, delete "contract" and replace with --contrast--

Column 10, Line 43, delete "contract" and replace with --contrast--

Column 11, Line 2, delete "MM" and replace with --MRI--

Column 11, Line 9, delete "contract" and replace with --contrast--

Signed and Sealed this
Eighteenth Day of April, 2017

Michelle K. Lee
*Director of the United States Patent and Trademark Office*

CERTIFICATE OF CORRECTION (continued)
U.S. Pat. No. 9,589,374 B1

Column 12, Line 9, delete "contract" and replace with --contrast--

Column 12, Line 44, delete "contract" and replace with --contrast--

Column 15, Line 66, delete "contract" and replace with --contrast--

In the Claims

Column 22, Line 58, Claim 4, delete "MM" and replace with --MRI--

Column 22, Line 67, Claim 6, delete "contract" and replace with --contrast--

Column 24, Line 8, Claim 27, delete "contract" and replace with --contrast--